United States Patent [19]

Spivack et al.

[11] Patent Number: 4,524,167
[45] Date of Patent: Jun. 18, 1985

[54] POLYMERIC HINDERED PHOSPHONATE STABILIZERS

[75] Inventors: John D. Spivack, Spring Valley; Stephen D. Pastor, Yonkers, both of N.Y.

[73] Assignee: Ciba-Geigy Corporation, Ardsley, N.Y.

[21] Appl. No.: 655,277

[22] Filed: Sep. 27, 1984

Related U.S. Application Data

[63] Continuation-in-part of Ser. No. 582,151, Feb. 24, 1984, abandoned, which is a continuation of Ser. No. 459,844, Jan. 21, 1983, abandoned.

[51] Int. Cl.³ .............. C08K 5/51; C07F 9/06; C08G 79/00
[52] U.S. Cl. .................. 524/121; 260/929; 260/930; 524/125; 524/128; 528/167
[58] Field of Search .......... 524/125, 121, 128; 260/929, 930; 528/167

[56] References Cited

U.S. PATENT DOCUMENTS

| 3,285,855 | 11/1966 | Dexter et al. | 524/291 |
|---|---|---|---|
| 3,655,832 | 4/1972 | Kauder et al. | 260/929 |
| 3,737,486 | 6/1973 | Schutze et al. | 524/127 |
| 3,932,566 | 1/1976 | Reader | 524/125 |
| 3,944,594 | 3/1976 | Kleiner et al. | 524/291 |
| 4,044,074 | 8/1977 | Walsh et al. | 260/930 |
| 4,094,855 | 6/1978 | Spivack . | |
| 4,117,042 | 9/1978 | Couchoud | 524/125 |
| 4,298,520 | 11/1981 | Minagawa et al. | 260/930 |

FOREIGN PATENT DOCUMENTS 1205211 2/1960 France .

Primary Examiner—Veronica P. Hoke
Attorney, Agent, or Firm—Luther A. R. Hall; Harry Falber

[57] ABSTRACT

Polymeric hindered secondary phosphonates which have the repeating structural unit of the formula

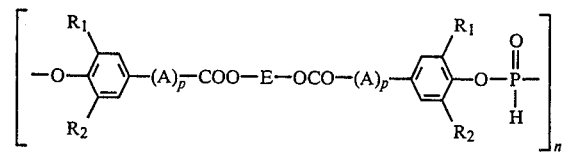

where $R_1$ and $R_2$ are independently alkyl, cycloalkyl, aralkyl or alkaryl, A is alkylene, E is alkylene or phenylene, p is 0 or 1 and n is 2 to 50 are useful as stabilizers for organic polymers to counteract the degradative effects of heat, light and air.

14 Claims, No Drawings

POLYMERIC HINDERED PHOSPHONATE STABILIZERS

This is a continuation-in-part of application Ser. No. 582,151, filed on Feb. 24, 1984, now abandoned, which in turn is a continuation of application Ser. No. 459,844, filed on Jan. 21, 1983, all now abandoned.

Organic polymeric materials such as plastics and resins, are subject to thermal, oxidative and photo-degradation. A great variety of stabilizers are known in the art for stabilizing a diversity of substrates. Their effectiveness varies depending upon the causes of degradation and the substrate stabilized. In general, it is difficult to predict which stabilizer will be most effective and most economical for any one area of application. For example, stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of disclororation may require inhibiting reactions which yield new chromophores or color bodies in the substrate or stabilizer. Problems of process stability and incompatibility must also be considered.

U.S. Pat. No. 3,737,486 describes polymeric polyphosphonates useful as antioxidants for polyolefins. These polyphosphonates are derived from bisphenols having structures very different from the bisphenol diesters precursors of the instant polyphosphonates.

U.S. Pat. No. 3,655,832 pertains to stabilizers which are phenolic phosphites. Polymeric phosphites are not described although a cyclic phosphite tetramer is disclosed. Phosphonates are not mentioned and the instant polymeric phosphonates differ structurally from the phosphites of this patent.

It has now been determined that the phosphonate derivatives of this invention possess an unusual combination of desirable properties which makes them particularly effective and useful as stabilizers. The compounds are particularly effective in protecting polyolefins, polyvinyl chloride, polyesters, high impact polystyrene, rubbers such as polybutadiene and styrenebutadiene rubber, and other polymers wherein inhibition of crosslinking, crazing, discoloration, odor formation and exudation are basic requirements.

It is the primary object of this invention to provide a class of polymeric phosphonates which exhibit a broad range of improved stabilization performance characteristics.

Various other objects and advantages of this invention will become evident from the following description thereof.

The polymeric phosphonates of this invention have the repeating structural unit of the formula

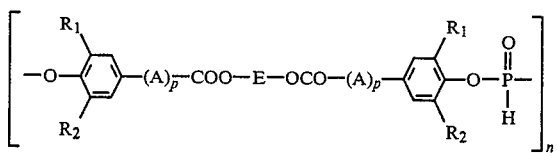

wherein $R_1$ and $R_2$ are independently alkyl of 4 to 12 carbon atoms, cycloalkyl of 5 to 6 carbon atoms, aralkyl of 7 to 15 carbon atoms, or alkaryl of 7 to 15 carbon atoms, A is alkylene of 1 to 4 carbon atoms, E is alkylene of 2 to 12 carbon atoms, phenylene, phenylene substituted by one or two alkyl groups of 1 to 9 carbon atoms; or is the group —T(OT)$_t$— where T is ethylene, propylene or 1,4-butylene, and t is 1 to 10; or is the group —G—X—G— where G is alkylene of 2 to 4 carbon atoms, and X is sulfur or —N(R)— where R is hydrogen or alkyl of 1 to 8 carbon atoms, p is 0 or 1; and n is 2 to 50.

The $R_1$ and $R_2$ group are preferably straight-chain or branched alkyl with 4 to 8 carbon atoms, such as n-butyl, sec-butyl, tert-butyl, tert-pentyl, 2-ethylhexyl, n-octyl and tert-octyl. The groups tert-butyl, tert-pentyl and tert-octyl are especially preferred. R is preferably alkyl of 1 to 4 carbon atoms. Aralkyl includes benzyl, and alkaryl includes tolyl, mesityl, xylyl and the like.

The A group is preferably a direct bond (i.e. p is 0) or alkylene of 1 to 2 carbon atoms such as ethylene.

E is preferably hexamethylene, 2,2-dimethyl-1,3-propanediyl or neopentylene, thiodiethylene and poly(oxyethylene) of 4 to 40 carbon atoms or —T(OT)$_t$— where T is ethylene and t is 1 to 10.

The phosphonates of this invention can be prepared by reacting the appropriately substituted bis-phenol

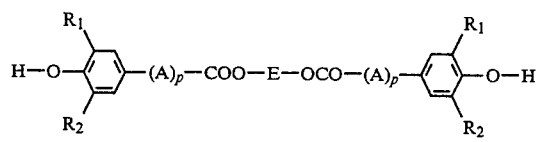

wherein the definitions of $R_1$, $R_2$, A, E and p are as previously set forth, with phosphorus trichloride in appropriate concentrations, optionally in a solvent system, to yield the desired polymeric product. The solvent system is preferably aromatic, such as benzene, toluene, xylene and the like, or a heterocyclic ether such as tetrahydrofuran, optionally in the presence of an aliphatic co-solvent such as heptane, hexane, and the like. The reaction temperature ranges from −5° C. to the reflux temperature of the reaction medium. The preferred method for preparing the polymers of this invention involves conduction the reaction in the presence of a proton acceptor such as a tertiary amine, for example, triethylamine or pyridine, or a metal hydride such as sodium hydride.

The starting phenol materials needed to prepare these polymeric phosphonates are items of commerce or can be prepared by known methods. A typical preparative procedure involves transesterification of a lower alkyl ester of a hindered phenolic carboxylic acid with the appropriate glycol.

Preferred bis-phenols include hexamethylene bis(3,5-di-tert-butyl-4-hydroxybenzoate), hexamethylene bis(3,5-di-tert-butyl-4-hydroxyhydrocinnamate), 2,2-dimethyl-1,3-propanediyl bis(3,5-di-tert-butyl-4-hydroxy-hydrocinnamate) and thiodiethylene bis(3,5-di-tert-butyl-4-hydroxyhydrocinnamate).

The presence of the two groups $R_1$ and $R_2$ on the ortho positions relevant to the phosphonate linkage is necessary for both the preparation and stability of the instant phosphonates.

The four groups, such as tert-butyl, provide hydrolytic stability to the polyphosphonates. It is noted that the intermediate polyphosphorochloridite, prepared by reaction of the bisphenol and phosphorus trichloride, is treated with water, usually in excess, over an extended period to convert the polychloridite to the corresponding polyphosphonate without any evidence of hydrolysis of the polyphosphonate.

Phosphonate compounds lacking the hindering groups on the ortho positon are hydrolyzed rapidly. (J. D. Spivack et al, Phosphorus Chemistry, Proc. 1981 International Conference, pp 351-354, A.C.S. Wash., D.C.)

Hydrolysis of phosphorus compounds, such as some phosphites, even during storage under ambient conditions of temperature and humidity leads to caking of the compound, to extrusion and spinning problems during processing of substrates stabilized by said compounds, to the corrosion of equipment and to the contamination of extrudate or fibers with hydrolysis and corrosion products, all of which are certainly undesired. (J. D. Spivack et al, 187th A.C.S. National Meeting, 1984, Division of Polymer Chemistry, 25, pp 72-73.)

Further evidence that the phosphorus atom of the instant polyphosphonate is truly hindered is seen in the fact that the methyl polyphosphorochloridite intermediate will not react with methyl alcohol, a relatively small molecule, to give a phosphite "related" to those of U.S. Pat. No. 3,655,832.

When the synthesis of polyphosphonates prepared from bisphenol esters having only one hindering group on the ortho positon to the hydroxy is attempted by the reaction of a 3-methyl-5-tert-butyl-4-hydroxy phenolic ester with phosphorus trichloride, a useless crosslinked polymer gel is formed indicating again the need for two ortho hindering groups on each phenolic moiety.

The polymers of this invention are effective in stabilizing organic materials such as plastics, polymers and resins. The polymers are particularly useful as stabilizers for the protection of polyolefins, for instance, polyethylene, polypropylene, polyisobutylene, poly(butene-1), poly(pentene-1), poly(3-methylbutene-1), poly(4-methyl-pentene-1), various ethylene-propylene copolymers and the like.

Other substrates in which the polymers of this invention are particularly useful are polyvinyl chloride, polystyrene, including impact polystyrene, ABS resin, SBR, polyisoprene, as well as natural rubber, polyesters including polyethylene terephthalate and polybutylene terephthalate, including copolymers, polyurethanes, polycarbonates, polyamides such as nylon 6, 6/6 and the like as well as copolyamides and polysulfones.

In general, polymers which can be stabilized include:
1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.
2. Mixtures of the polymers mentioned under (1), for example mixtures of polypropylene with polyethylene or with polyisobutylene.
3. Copolymer of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/ethyl acrylate, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene norbornene.
4. Polystyrene.
5. Random copolymers of styrene of α-methylstyrene with dienes or acrylic derivatives, such as, for example, styrene/butadiene, styrene/acrylonitrile, styrene/alkyl methacrylates, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene.
6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.
7. Halogen-containing polymers, such as polychloroprene, chlorinated rubbers, chlorinated or sulfochlorinated polyethylene, polymers from halogen-containing vinyl compounds, as for example, polyvinyl chloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.
8. Polymers which are derived from α,β-unsaturated acids and derivatives thereof, such as polyacrylates and polymethacrylates, polyacrylamides and polyacrylonitrile.
9. Copolymers from the monomers mentioned under (8) with each other or with other unsaturated monomers, such as, for instance, acrylonitrile/butadiene, acrylonitrile/alkyl acrylate or acrylonitrile/vinyl chloride copolymers or acrylonitrile/alkyl methacrylate/butadiene terpolymers.
10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallylmelamine.
11. Homopolymers and copolymers of cyclic ethers, such as polyalkylene glycols, polyethylene oxide, polypropylene oxide or copolymers thereof with bis-glycidyl ethers.
12. Polyacetals, such as polyoxymethylene and those polyoxymethylenes which contain ethylene oxide as a comonomer.
13. Polyphenylene oxides and sulfides.
14. Polyurethanes which are derived from polyethers, polyesters or polybutadienes with terminal hydroxyl groups on the one side and aliphatic or aromatic polyisocyanates on the other side, as well as precursors thereof.
15. Polyamides and copolyamides which are derived from diamines and dicarboxylic acids and/or from aminocarboxylic acids of the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance, with polyethylene glycol, polypropylene glycol or polytetramethylene glycols.

16. Polyureas, polyimides and polyamide-imides.
17. Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate and polyhydroxybenzoates as well as block copolyether-esters derived from polyethers having hydroxyl end groups.
18. Polycarbonates.
19. Polysulfones and polyethersulfones.
20. Crosslinked polymers which are derived from aldehydes on the one hand and phenols, ureas and melamines on the other hand, such as phenol/formaldehyde resins, urea/formaldehyde resins and melamine/formaldehyde resins.
21. Drying and non-drying alkyd resins.
22. Unsaturated polyester resins which are derived from copolyesters of saturated and unsaturated dicarboxylic acids with polyhydric alcohols and vinyl compounds as crosslinking agents, and also halogen-containing modifications thereof of low flammability.
23. Thermosetting acrylic resins, derived from substituted acrylic esters, such as epoxy-acrylates, urethane-acrylates or polyester-acrylates.
24. Alkyd resins, polyester resins or acrylate resins in admixture with melamine resins, urea resins, polyisocyanates or epoxide resins as crosslinking agents.
25. Crosslinked epoxide resins which are derived from polyepoxides, for example from bis-glycidyl ethers or from cycloaliphatic diepoxides and aromatic diepoxides.
26. Natural polymers, such as cellulose, rubber, gelatin and derivatives thereof which are chemically modified in a polymer-homologous manner, such as cellulose acetates, cellulose propionates and cellulose butyrates, or the cellulose ethers, such as methylcellulose.
27. Naturally occurring and synthetic organic materials which are pure monomeric compounds or mixtures of such compounds, for example mineral oils, animal and vegetable fats, oils and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.
28. Aqueous emulsions of natural or synthetic rubber, e.g. natural latex or latices of carboxylated styrene-/butadiene copolymers.

In general, the stabilizers of this invention are employed in from about 0.01 to about 5% by weight of the stabilized composition, although this will vary with the particular substrate and application. An advantageous range is from about 0.05 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following:

1. Antioxidants 1.1 Simple 2.6-dialkylphenols, such as, for example, 2,6-di-tert.-butyl-4-methylphenol, 2-tert.-butyl-4,6-dimethylphenol, 2,6-di-tert.-butyl-4-methoxymethylphenol and 2,6-di-octadecyl-4-methylphenol.

1.2. Derivatives of alkylated hydroquinones, such as, for example, 2,5-di-tert.-butyl-hydroquinone, 2.5-di-tert.-amylhydroquinone, 2,6-di-tert.-butyl-hydroquinone, 2,6-di-tert.-butyl-4-hydroxy-anisole, 3,5-di-tert.-butyl-4-hydroxy-anisole, tris-(3,5-di-tert.-butyl-4-hydroxyphenyl)phosphite, 3,5-di-tert.-butyl-4-hydroxyphenyl stearate and bis-(3,5-di-tert.-butyl-4-hydroxyphenyl)adipate.

1.3. Hydroxylated thiodiphenyl ethers, such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl)disulphide.

1.4. Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol), 4,4'-methylene-bis-(2,6-di-tert.-butyl-phenol), 2,6-di-(3-tert.-butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercapto-butane, 1,1,5,5-tetra-(5-tert.-butyl-4-hydroxy-2-methylphenyl)-pentane and ethylene glycol bis-[3,3-bis-(3'-tert.-butyl-4'-hydroxyphenyl)-butyrate].

1.5. O-, N- and S-benzyl compounds, such as, for example, 3,3',5,5'-tetra-tert.-butyl-4,4'-dihydroxydibenzyl ether, octadecyl 4-hydroxy-3,5-dimethylbenzyl-mercaptoacetate, tris-(3,5-di-tert.-butyl-4-hydroxybenzyl)-amine and bis-(4-tert.-butyl-3-hydroxy-2,6-dimethylbenzyl)dithioterephthalate.

1.6. Hydroxybenzylated malonates, such as, for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)-phenyl] 2,2-bis-(3,5-di-tert.-butyl-4-hydroxybenzyl)-malonate.

1.7. Hydroxybenzyl-aromatic compounds, such as, for example, 1,3,5-tris-(3,5-di-tert.-butyl-4-hydroxybenzyl)-2,4,6-trimethylbenzene, 1,4-bis-(3,5-di-tert.-butyl-4-hydroxybenzyl)-2,3,5,6-tetramethylbenzene and 2,4,6-tri-(3,5-di-tert.-butyl-4-hydroxybenzyl)-phenol.

1.8. s-Triazine compounds, such as, for example, 2,4-bis-octylmercapto-6-(3,5-di-tert.-butyl-4-hydroxyanilino)-s-triazine, 2-octylmercapto-4,6-bis-(3,5-di-tert.-butyl-4-hydroxyanilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert.-butyl-4-hydroxyphenylethyl)-s-triazine and 1,3,5-tris-(3,5-di-tert.-butyl-4-hydroxybenzyl)isocyanurate.

9. Amides of β-(3,5-di-tert.-butyl-4-hydroxyphenyl)propionic acid, such as, for example, 1,3,5-tris-3,5-di-tert.-butyl-4-hydroxyphenyl-propionyl)-hexahydro-s-triazine and N,N'-di-(3,5-di-tert.-butyl-4-hydroxyphenyl-propionyl)-hexamethylenediamine. N,N'-bis-β-(3,5-di-t-butyl-4-hydroxyphenylpropionyl)-hydrazine.

1.10. Esters of β-(3,5-di-tert.-butyl-4-hydroxyphenyl)-propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, triethylene glycol, thiodiethylene glycol, neopentylglycol, pentaerythritol, 3-thia-undecanol, 3-thiapentadecanol, trimethylhexanediol, trimethylolethane, trimethylolpropane, tris-hydroxyethyl isocyanurate and 4-hydroxymethyl-1-phospha-2,6,7-trioxabicyclo-[2,2,2]octane.

1.11. Esters of β(5-tert.-butyl-4-hydroxy-3-methylphenyl)propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, triethylene glycol, thiodiethylene glycol, neopentylglycol, pentaerythritol, 3-thia-undecanol, 3-thiapentadecanol, trimethylhexanediol trimethylolethane, trimethylolpropane, tris-hydroxyethyl isocyanurate and 4-hydroxymethyl-1-phospha-2,6,7-trioxabicyclo[2,2,2]octane.

1.12. Esters of 3,5-di-tert.-butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiglycol, neopentylglycol, pentaerythritol, 3-thia-undecanol, 3-thiapentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]-octane, especially the tetra-bis ester of pentaerythritol.

1.13. Benzylphosphonates, such as, for example, dimethyl 3, 5-di-tert.-butyl-4-hydroxybenzyl-phosphonate, diethyl 3,5-di-tert.butyl-4-hydroxybenzyl-phosphonate, dioctadecyl 3,5-di-tert.butyl-4-hydroxybenzyl-phosphonate and dioctadecyl 5-tert.-butyl-4-hydroxy-3-methylbenzyl-phosphonate.

The following may be mentioned as examples of further additives that can be used together with the stabilizer of this invention and the antioxidant:

1. Aminoaryl derivatives, e.g. phenyl-1-naphthylamine, phenyl-2-naphthylamine, N,N'-diphenyl-p-phenylenediamine, N,N'-di-2-naphthyl-p-phenylenediamine, N,N'-di-naphthyl-p-phenylenediamine, N,N'-di-sec.butyl-p-phenylenediamine, 6-ethoxy-2,2,4-trimethyl-1,2-dihydroquinoline, 6-dodecyl-2,2,4-trimethyl-1,2-dihydroquinoline, mono- and dioctyliminodibenzyl, polymerized 2,2,4-trimethyl-1,2-dihydroquinoline.

Octylated diphenylamine, nonylated diphenylamine, N-phenyl-N'-cyclohexyl-p-phenylenediamine, N-phenyl-N'-isopropyl-p-phenylenediamine, N,N'-di-sec.octyl-p-phenylenediamine, N-phenyl-N'-sec.-octyl-p-phenylenediamine, N,N'-di-(1,4-dimethylpentyl)-p-phenylenediamine, N,N'-dimethyl-N,N'-di-(sec.-octyl)-p-phenylenediamine, 2,6-dimethyl-4-methoxyaniline, 4-ethoxy-N-sec.-butylaniline, diphenylamineacetone condensation product, aldol-1-naphthylamine and phenothiazine.

Discoloration effects have to be taken into account when using the above antioxidants.

2. UV-Absorbers and light-stabilising agents 2.1. 2-(2'-Hydroxyphenyl)-benzotriazoles, e.g. the 5'-methyl-, 3',5'-di-tert.-butyl-, 5'-tert.butyl-, 5'-(1,1,3,3-tetramethylbutyl)-, 5-chloro-3',5'-di-tert.-butyl-, 5-chloro-3'-tert.-butyl-5'-methyl-, 3'-sec.-butyl-5'-tert.-butyl-, 3'-alpha-methylbenzyl-5'-methyl-, 3'-alpha-methylbenzyl-5'-methyl-5-chloro-, 4'-hydroxy-, 4'-methoxy-, 4'-octoxy-, 3',5'-di-tert.-amyl-, 3'-methyl-5'-carbomethoxyethyl-, 3',5'-bis(alpha,alpha-dimethylbenzyl),3',5'-bis(alpha,alpha-dimethyl benzyl)-5-chloro-, 3',5'-di-tert.-octylphenyl, 3',5'-di-tert.-octylphenyl-5-chloro- and 5-chloro-3',5'-di-tert.-amyl-derivatives.

2.2. 2,4-bis-(2'-Hydroxyphenyl)-6-alkyl-s-triazines, e.g. the 6-ethyl-, 6-heptadecyl- or 6-undecyl-derivative.

2.3. 2-Hydroxybenzophenones, e.g. the 4-hydroxy-, 4-methoxy-, 4-octoxy-, 4-decyloxy-, 4-dodecyloxy-, 4-benzyloxy-, 2',4-4'-trihydroxy- or 2'-hydroxy-4,4'-dimethoxy-derivative.

2.4. 1,3-bis-(2'-Hydroxybenzoyl)-benzenes, e.g. 1,3-bis-(2'-hydroxy-4'-hexyloxy-benzoyl)-benzene, 1,3-bis-(2'-hydroxy-4'-octyloxy-benzoyl)-benzene or 1,3-bis-(2'-hydroxy-4'dodecyloxy-benzoyl)-benzene.

2.5. Esters of optionally substituted benzoic acids, e.g. phenylsalicylate, octylphenylsalicylate, dibenzoylresorcin, bis-(4-tert.-butylbenzoyl)-resorcin, benzoylresorcin, 3,5-di-tert.-butyl-4-hydroxybenzoic acid-2,4-di-tert.-butylphenyl ester or -octadecyl ester of -2-methyl-4,6-di-tert.-butyl ester.

2.6. Acrylates, e.g. α-cyano-β,β-diphenylacrylic acid-ethyl ester or -isooctyl ester, α-carbomethoxy-cinnamic acid methyl ester, α-cyano-β-methyl-p-methoxy-cinnamic acid methyl ester or butyl ester or N-(β-carbomethoxyvinyl)-2-methyl-indoline.

2.7. Sterically hindered amines, e.g. 4-benzoyl-2,2,6,6-tetramethylpiperidine, 4-stearyl-oxy-2,2,6,6-tertramethylpiperidine, bis-(2,2,6,6-tetramethylpiperidyl)-sebacate or 3-n-octyl-7,7,9,9-tetramethyl-1,3,3-triazaspiro[4,5]decane-2,4-dione.

2.8. Oxalic acid diamides, e.g. 4,4'-di-octyloxy-oxanilide, 2,2'-di-dodecyloxy-5,5'-di-tert.-butyl-oxanilide, 2-ethoxy-2'-ethyl-oxanilide, N,N'-bis-(3-dimethylaminopropyl)-oxalamide, 2-ethoxy-5-tert.-butyl-2'-ethyl-5,4'-di-tert.-butyl-oxanilide, or mixtures of ortho- and para-methoxy- as well as of o- and p-ethoxy-disubstituted oxanilides.

3. Metal deactivators, e.g. oxanilide, isophthalic acid dihydrazide, sebacic acid-bis-phenylhydrazide, bis-benzylidene-oxalic acid dihydrazide, N,N'-diacetyl-adipic acid dihydrazide, N,N'-bis-salicyloyloxalic acid dihydrazide, N,N'-bis-salicyloylhydrazine, N,N'-bis-(3,5-di-tert.-butyl-4-hydroxyphenylpropionyl)-hydrazine, N-salicyloyl-N'-salicylalhydrazine, 3-salicyloyl-amino-1,2,4-triazole or N,N'-bis-salicyloyl-thiopropionic acid dihydrazide.

4. Basic co-stabilisers, e.g. alkali metal salts and alkaline-earth metal salts of higher fatty acids, for example Ca-stearate, Zn-stearate, Mg-behenate, Na-ricinoleate or K-plamitate.

5. Nucleation agents, e.g. 4-tert.-butylbenzoic acid, adipic acid or diphenylacetic acid.

6. Phosphites, such as, for example, triphenyl phosphite, diphenylalkyl phosphites, phenyldialkyl phosphites, tri-(nonylphenyl)phosphite, trilauryl phosphite, trioctadecyl phosphite, 3,9-isodecyloxy-2,4,8,10-tetraoxa-3,9-diphospha spiro[5,5]-undecane and tri-(4-hydroxy-3,5-di-tert.-butylphenyl)phosphite.

Other additives that can be incorporated in the stabilized compositions are thiosynergists such as dilaurylthiodipropionate or distearylthiodipropionate, lubricants such as stearyl alcohol fillers, carbon black, asbestos, kaolin, talc, glass fibers, pigments, optical brighteners, flameproofing agents and antistatic agents.

The compounds of this invention may be used alone as the sole stabilizer having either mainly an antioxidant function or a light stabilizing function or the stabilizer may combine utility as an antioxidant and light stabilizer. The stabilizers may be used with phenolic antioxidants, lubricants such as calcium stearate, pigments, colorants or dyes, UV absorbers, light stabilizers such as hindered amines, metal deactivators, talc and other fillers, etc.

While the instant compounds can be beneficially used as stabilizers for a variety of substrates both alone and in conjunction with other coadditives, the combination of the instant compounds with selected hindered phenolic antioxidants exhibits enhanced protection of such substrates. The phenolic antioxidants found to be particularly useful are selected from the group consisting of 2,6-di-tert-butyl-4-methylphenol, 4,4'-thio-bis(6-tert.-butyl-3-methylphenol), 2,2'-methylene-bis(6-tert.-butyl-3-methylphenol), 4,4'-methylene-bis-(2,6-di-tert.-butylphenol), 1,1,3-tris(5-tert.-butyl-4-hydroxy-2-methylphenyl)butane, 1,3,5-tris(3,5-di-tert.-butyl-4-hydroxybenzyl)-2,4,6-trimethylbenzene, 2-octylthio-4,6-bis(3,5-di-tert-butyl-4-hydroxyanilino)-s-triazine, n-octadecyl 3,5-di-tert-butyl-4-hydroxyhydrocinnamate, neopentanetetrayl tetrakis(3,5-di-tert.-butyl-4-hydroxy hydrocinnamate), 1,3,5-tris(3,5-di-tert.butyl-4-hydroxybenzyl)isocyanurate, thiodiethylene bis-(3,5-di-tert-butyl-4-hydroxy hydrocinnamate), tris-(2-hydroxyethyl)isocyanurate ester of β-(3,5-di-tert-butyl-4-hydroxyphenyl)propionic acid, 6,6'-ethylidene-bis(2,4-di-tert-.butyl phenol), 6,6'-methylene-bis(2,4-di-tert.butylphenol) and 1,3,5-tris(4-tert.butyl-3-hydroxy-2,6-dimethylbenzyl)isocyanurate.

The compositions comprise (a) a substrate, preferably a polyolefin such as polypropylene, (b) about 0.01 to about 5% by weight of the composition and preferably about 0.025 to about 2%, and most preferably 0.025 to 1% of an instant compound or mixture thereof, and optionally, (c) a phenolic antioxidant or mixture of said antioxidants selected from the group cited directly above and also in a range of 0.01 to 5% and preferably 0.05 to 1%, by weight of the composition.

Likewise, the following light stabilizers are preferred for use, either alone or in conjunction with the listed phenolic antioxidants, as additives for incorporation with the instant stabilizers into the listed substrates: 2-(2'-hydroxy-5'-methylphenyl)benzotriazole; 2-(3',5'-di-tert-butyl-2'-hydroxyphenyl)benzotriazole; 2-(2'-hydroxy-3',5'-di-tert-amylphenyl)benzotriazole; nickel bis[O-ethyl-(3,5-di-tert-butyl-4-hydroxybenzyl)]phosphonate; bis(1,2,2,6,6-pentamethyl-4-piperidyl)-2-n-butyl-2-(3,5-di-tert-butyl-4-hydroxybenzyl)malonate; bis(2,2,6,6-tetramethyl-4-piperidyl)sebacate; dimethylsuccinate polymer with 4-hydroxy-2,2,6,6-tetramethyl-1-piperidinethanol; and polymer of 2,4-dichloro-6-octylamino-s-triazine with N'-(2,2,6,6-tetramethyl-4-piperidyl)hexamethylene diamine.

The following examples further illustrate the embodiments of this invention. In these examples, all parts given are by weight unless otherwise specified.

EXAMPLE 1

Poly[hexamethylene bis(4-(3,5-di-tert-butyl)benzoate) phosphonate]

A solution of 2.74 grams phosphorus trichloride and 4.29 grams triethylamine in 200 ml toluene is charged into a flask under a nitrogen atmosphere and is treated with a solution of 11.64 grams hexamethylene bis(3,5-di-tert-butyl-4-hydroxybenzoate) in 100 ml toluene at 10° C. The reaction mixture is stirred 48 hours at ambient temperature, treated with 0.18 grams water and 0.87 grams pyridine, heated to 50° C. for 24 hours and filtered to remove amine hydrochloride. The volatiles are then removed in vacuo. The residue is purified by dry column chromatography to give a white solid, mp 76°–89° C. IR: (1% in chloroform) 1475 cm$^{-1}$ (P-H).

Analysis: Calculated for [$C_{36}H_{53}O_7P$]n: C, 68.6; H, 8.50; P, 4.93. Found: C, 69.52; H, 8.70; P, 4.05.

Gel permeation chromatographic analysis: n=2–4.

EXAMPLE 2

Poly[hexamethylenebis(4-(3,5-di-tert-butyl)benzoate)-phosphonate]

A lower molecular weight copolymer is prepared by the procedure of Example 1 using 1.37 grams phosphorus trichloride, 2.12 grams triethylamine, 11.66 grams hexamethylene bis(3,5-di-tert-butyl-4-hydroxybenzoate), 0.79 grams pyridine, and 0.18 grams water. The residue is purified by dry column chromatography to give a white solid, m.p. 68°–78° C. IR: (1% in chloroform) 1475 cm$^{-1}$(P-H).

Analysis: Calculated for [$C_{36}H_{53}O_7P$]n: C, 68.76; H, 8.50; P, 4.93. Found: C, 70.60; H, 9.01; P, 3.38.

Gel permeation chromatographic analysis: n=2–3.

EXAMPLE 3

Poly[hexamethylenebis(4-(3,5-di-tert-butyl)benzoate)-phosphonate]

This example illustrates the preparation of a higher molecular weight copolymer.

A solution of 29.1 grams hexamethylene bis(3,5-di-tert-butyl-4-hydroxybenzoate) in 300 ml tetrahydrofuran is charged into a flask under nitrogen and is treated with a suspension of 2.4 grams sodium hydride in 100 ml tetrahydrofuran. The reaction mixture is heated to 60° C. for two hours, cooled to 5° C., and the resultant white suspension treated slowly with 6.87 grams phosphorus trichloride. The reaction is stirred at ambient temperature for 24 hours, cooled to 15° C., treated with 1.8 grams water and 4.0 grams pyridine, and stirred for 24 hours at ambient temperature. The reaction mixture is then filtered, the solvent removed in vacuo, and the residue purified by dry column chromatography to give a white solid, m.p. 95°–110° C. IR: (1% in chloroform) 2450 cm$^{-1}$ (P-H).

Analysis: Calculated for [$C_{36}H_{53}O_7P$]n: C, 68.76; H, 8.50; P, 4.93. Found C, 68.81; H, 8.49; P, 4.15.

Gel permeation chromatographic analysis: n=3–5.

EXAMPLE 4

Poly[hexamethylenebis(4-(3,5-di-tert-butyl)hydrocinnamate)phosphonate]

The procedure of Example 3 is repeated using 15.97 grams hexamethylene bis(3,5di-tert-butyl-4-hydroxyhydrocinnamate), 1.2 grams sodium hydride, 1.72 grams phosphorus trichloride, 1.8 grams water, and 0.99 grams of pyridine. The residue was purified by dry column chromatography to give a white solid, m.p. 45°–49° C. IR: (1% in carbon tetrachloride) 2450 cm$^{-1}$ (P-H).

Analysis calculated for $[C_{40}H_{61}O_7P]n$: C, 70.15; H, 8.98; P, 4.52. Found: C, 71.70; H, 9.15; P, 2.94.

Gel permeation chromatographic analysisl: n=2–12.

EXAMPLE 5

Poly[hexamethylenebis(4-(3,5-di-tert-butyl)hydrocinnamate)phosphonate]

This example illustrates the preparation of a copolymer of Example 4 having, in this instance, a higher molecular weight. The procedure of Example 3 is repeated using 63.90 grams hexamethylene bis(3,5-di-tert-butyl-4-hydroxyhydrocinnamate), 4.30 grams sodium hydride, 13.73 grams phosphorus trichloride, 3.60 grams water, and 7.91 grams pyridine. The residue is purified by dry column chromatography to give a white powder, m.p. 61°–69° C. IR: (1% in carbon tetrachloride) 2450 cm$^{-1}$ (P-H).

Analysis: Calculated for $[C_{40}H_{61}O_7P]n$: C, 70.15; H, 8.98; P, 4.52. Found C, 71.54; H, 8.82; P, 3.31.

EXAMPLE 6

Poly[2,2-dimethyl-1,3-propanediylbis(4-(3,5-di-tert-butyl)hydrocinnamate)phosphonate]

The procedure of Example 3 is repeated using 62.49 grams 2,2-dimethyl-1,3-propanediyl bis(3,5-di-tert-butyl-4-hydroxyhydrocinnamate), 4.8 grams sodium hydride, 13.73 grams phosphorus trichloride, 3.6 grams water, and 7.91 grams pyridine. The residue is purified by dry column chromatography to give a white powder, m.p. 70°–80° C. IR: (1% in carbon tetrachloride) 2450 cm$^{-1}$ (P-H).

Analysis: Calculated for $[C_{39}H_{59}O_7P]n$: C, 69.82; H, 8.86; P, 4.62. Found: C, 69.94; H, 9.20; P, 4.02.

EXAMPLE 7

Poly[thiodiethylenebis(4-(3,5-di-tert-butyl)hydrocinnamate)phosphonate]

The procedure of Example 3 is repeated using 100 grams thiodiethylene bis(3,5-di-tert-butyl-4-hydroxyhydrocinnamate), 7.49 sodium hydride, 21.42 grams phosphorus trichloride, 5.62 grams water, and 15.80 grams triethylamine in place of pyridine. The residue is purified by dry column chromatography to give a white powder, m.p. 52–64. IR: (1% in carbon tetrachloride) 2450 cm$^{-1}$ (P-H).

Analysis: Calculated for $[C_{38}H_{57}O_7PS]n$: C, 66.25; H, 8.34; P, 4.50; S, 4.65. Found: C, 65.10; H, 8.11; P, 3.72; S, 4.90.

EXAMPLE 8

Unstabilized polypropylene powder (Hercules Profax 6501) is thoroughly blended with the indicated amount of additives. The blended materials are then milled on a two-roll mill at 182° C. for 5 minutes, after which time the stabilized polypropylene was sheeted from the mill and allowed to cool. The milled polypropylene is then cut into pieces and compression molded on a hydraulic press at 220° C. and 175 psi (1.2×10$^6$ Pa) into 25 mil (0.635 mm) thick plaques. Representative samples are exposed in a fluorescent sunlight/black light chamber and oven aged at 150° C. with the time to failure being determined in each instance. Failure is evidenced by the first crazing and discoloration of the exposed plaques.

| | Oven Aging at 150° C. | |
|---|---|---|
| Additive | Antioxidant A (% by weight) | Time to Failure (hours) |
| None | — | <20 |
| 0.1% Polymer of Example 3 | — | 110 |
| 0.3% Polymer of Example 4 | — | 410 |
| 0.3% Polymer of Example 5 | — | 1030 |
| 0.3% Polymer of Example 5 | 0.1 | 1600 |
| 0.3% Polymer of Example 6 | — | 530 |
| 0.3% Polymer of Example 6 | 0.1 | 1440 |
| 0.2% Polymer of Example 7 | — | 890 |
| 0.3% Polymer of Example 7 | — | 1110 |
| 0.3% Polymer of Example 7 | 0.1 | 1520 |
| 0.1% Polymer of Example 7 and 0.3% of distearyl thiodipropanoate | — | 1190 |

Antioxidant A = Pentaerythrityl tetrakis [3-(3,5-di-t-butyl-4-hydroxyphenyl)propionate]

| | FS/BL Exposure | |
|---|---|---|
| Additive | Co-Additive B (%) | Time to Failure (hours) |
| None | 0.2 | 400 |
| 0.25% Polymer of Example 1 | 0.2 | 1080 |
| 0.25% Polymer of Example 3 | 0.2 | 1010 |
| 0.3% Polymer of Example 3 | — | 1000 |
| 0.25% Polymer of Example 4 | 0.2 | 450 |
| 0.25% Polymer of Example 5 | 0.2 | 600 |
| 0.2% Polymer of Example 7 | — | 400 |
| 0.3% Polymer of Example 7 | — | 1100 |

Co-Additive B-O,O-di-n-octadecyl 3,5-di-tert-butyl-4-hydroxy-benzylphosphonate.

EXAMPLE 9

Polypropylene (Hercules Profax 6501) containing 0.1% by weight of calcium stearate, but no antioxidant, is blended with the indicated concentration of stabilizers. The mixtures are pelletized and extruded at 232° C. into tape with a thickness of 0.127 mm, using a 10.16 cm film die. The tape is cut into 6.4 mm wide strips which are then stretched by a 6:1 ratio over Godet rolls at a temperature of 107° C. to give a stretched film tape of 0.0508 mm thickness.

The tapes are subjected to light exposure in the Carbon Arc Weatherometer (with spray). After exposure, specimen tensile properties are determined utilizing an Instron tensile strength tester. The hours in the Carbon Arc Weatherometer which resulted in a 50% reduction of tensile strength are considered as the failure time.

Correspondingly, sample tapes are oven aged at 125° C. The time to failure is determined in each instance based on the first appearance of crazing and discoloration.

| Additive | Carbon Arc Weatherometer (hours) | Oven Aging (hours) |
|---|---|---|
| 0.1% Polymer of Example 1 | 387 | 24 |

-continued

| Additive | Carbon Arc Weatherometer (hours) | Oven Aging (hours) |
|---|---|---|
| 0.1% Polymer of Example 2 | 931 | 237 |
| 0.1% Polymer of Example 3 | 754 | 238 |
| 0.1% Polymer of Example 4 | 375 | 591 |
| 0.1% Polymer of Example 6 | 736 | 264 |

These results indicate the effective heat and light stability provided by the instant stabilizers.

EXAMPLE 10

PVC resin (Geon 85862 from B. F. Goodrich-natural powder) containing a butyl tin mercaptide thermal stabilizer, but no $TiO_2$, is blended with 5 phr of a rutile grade of $TiO_2$. This formulation is noted as control (A). Thereafter, 1 phr of the polymer of Example 3 is added to a sample of (A) to yield formulation (B). Both formulations are molded in a two-roll mill at 170° C. and compression molded test plaques (20 mil thick) are made and tested by accelerated aging for 2000 hours in a Xenon Weatherometer. The yellowness index color of the plaques of (A) and (B) is determined by means of ASTM D-1925-63T. The results are noted in the following table.

| Formulation | Yellowness Index Initial | Yellowness Index 2000 Hours |
|---|---|---|
| A (control) | 5.3 | 18.6 |
| B | 5.1 | 9.5 |

These results clearly indicate the effectiveness of the instant stabilizers in reducing oxidation degradation.

EXAMPLE 11

Hydrolytic Stability

A compound or polymer must be stable at ambient temperature and under a variety of humidity conditions if it is to achieve any practical utility as a stabilizer since said compound or polymer may well be stored under such ambient conditions for extended periods.

If a compound or polymer hydrolyzes under such storage conditions, it certainly will be useless as a practical stabilizer since the hydrolysis will have converted the compound or polymer into other chemical species no longer possessing the stabilization efficacy of the original material.

Polyphosphonates of the instant invention have four hindering groups on the ortho positions adjacent to the phosphonate linkages. These exhibit excellent hydrolytic stability as seen in the table below.

Polyphosphonates with only two such hindering groups on the ortho positions of two separate phenyl rings and polyphosphonates with no such hindering groups at all are easily hydrolyzed, particularly the latter polyphosphonate.

Small samples (0.5 g) of the polyphosphonates being tested are placed in a Petri dish and weighed on an analytical balance. The dish is then placed in a desiccator kept at 80% relative humidity at room temperature for from 1 to 38 days. The dish is weighed periodically. The increase in weight observed is correlated to water absorption (pick-up) by the sample and is a relative measure of the amount of hydrolysis which has occurred.

The results are seen in the table below:
Hydrolytic Stability (80% R.H. @ r.t.)

| Polyphosphonate of | (Days under Test) | | | | | | |
|---|---|---|---|---|---|---|---|
| | 1 | 2 | 5 | 9 | 24 | 33 | 38 |
| A* | 15 | 17 | <20 | — | — | — | — |
| B* | 0.3 | 0.6 | 2.7 | 5.6 | 10.2 | 11.7 | 12.1 |
| Example 6 | 2.3 | 2.2 | 2.8 | 2.8 | 3.1 | 3.3 | 3.4 |
| Example 7 | 0.8 | 0.8 | 1.3 | 1.6 | 2.8 | 2.9 | 3.4 |
| Example 5 | 0.5 | 0.5 | 0.8 | 0.9 | 1.6 | 1.9 | 2.0 |
| Example 2 | 0.0 | 0.0 | 0.0 | 0.0 | 0.0 | 0.9 | 0.9 |

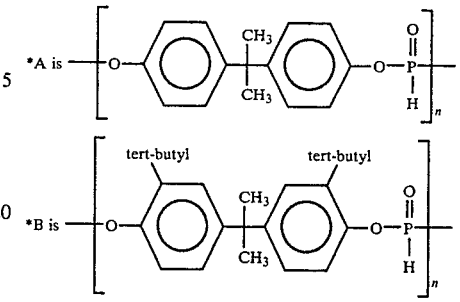

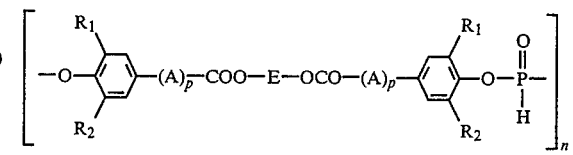

The instant polyphosphonates are resistant to hydrolysis while the unhindered or less hindered polyphosphonates A and B of the prior art are easily hydrolyzed.

Summarizing, this invention is seen to provide novel polymeric phosphonates which are especially effective in counteracting the degradative effects of heat, light and air. Variations may be made in proportions, procedures and materials without departing from the scope of the invention as defined by the following claims.

What is claimed is:

1. A polymeric phosphonate having the repeating structural unit of the formula $$\left[ -O-\underset{R_2}{\underset{|}{\bigcirc}}\overset{R_1}{\overset{|}{-}}(A)_p-COO-E-OCO-(A)_p-\underset{R_2}{\underset{|}{\bigcirc}}\overset{R_1}{\overset{|}{-}}O-\overset{O}{\underset{H}{\overset{\|}{P}}}- \right]_n$$

wherein
R$_1$ and R$_2$ are independently alkyl of 4 to 12 carbon atoms, cycloalkyl of 5 to 6 carbon atoms, or aralkyl of 7 to 15 carbon atoms, or alkaryl of 7 to 15 carbon atoms,
A is alkylene of 1 to 4 carbon atoms,
E is alkylene of 2 to 12 carbon atoms, phenylene, phenylene substituted by one or two alkyl groups of 1 to 9 carbon atoms; or is the group —T(OT)$_t$— where T is ethylene, propylene or 1,4-butylene, and t is 1 to 10; or is the group —G—X—G— where G is alkylene of 2 to 4 carbon atoms, and X is sulfur or —N(R)— where R is hydrogen or alkyl of 1 to 8 carbon atoms,
p is 0 or 1; and
n is 2 to 50.

2. A polymer according to claim 1, wherein R$_1$ and R$_2$ are tert-butyl.

3. A polymer according to claim 1, wherein p is 0 or where A is ethylene.

4. A polymer according to claim 1, wherein E is hexamethylene, thiodiethylene, 2,2-dimethyl-1,3-propanediyl or —T(OT)$_t$— where T is ethylene and t is 1 to 10.

5. Poly[hexamethylenebis(4-(3,5-di-tert-butyl)-benzoate)phosphonate] according to claim 1.

6. Poly[hexamethylenebis(4-(3,5-di-tert-butyl)hydrocinnamate)phosphonate] according to claim 1.

7. Poly[2,2-dimethyl-1,3-propanediylbis(4-(3,5-di-tert-butyl)hydrocinnamate)phosphonate] according to claim 1.

8. Poly[thioethylenebis(4-(3,5-di-tert-butyl)hydrocinnamate)phosphonate] according to claim 1.

9. A composition of matter comprising an organic material subject to oxidative, thermal and actinic degradation stabilized with an effective stabilizing amount of a polymer according to claim 1.

10. A composition according to claim 9, wherein the organic material is a synthetic polymer.

11. A composition according to claim 10, wherein said synthetic polymer is a polyolefin homopolymer or copolymer.

12. A composition according to claim 10, wherein said synthetic polymer is poly(vinyl chloride).

13. A composition according to claim 9, which also contains a phenolic antioxidant selected from the group consisting of 2,6-di-tert-butyl-4-methylphenol, 4,4′-thiobis(6-tert-butyl-3-methylphenol), 2,2′-methylene-bis(6-tert-butyl-3-methylphenol), 4,4′-methylene-bis(2,6-di-tert-butylphenol), 1,1,3-tris(5-tert-butyl-4-hydroxy-2-methylphenyl)butane, 1,3,5-tris(3,5-di-tert-butyl-4-hydroxybenzyl)-2,4,6-trimethylbenzene, 2-octylthio-4,6-bis(3,5-di-tert-butyl-4-hydroxyanilino)-s-triazine, n-octadecyl 3,5-di-tert-butyl-4-hydroxyhydrocinnamate, neopentanetetrayl tetrakis(3,5-di-tert-butyl-4-hydroxyhydrocinnamate), 1,3,5-tris(3,5-di-tert-butyl-4-hydroxybenzyl)isocyanurate, thiodiethylene bis(3,5-di-tert-butyl-4-hydroxyhydrocinnamate), tris(2-hydroxyethyl) isocyanurate ester of $\beta$-(3,5-di-tert-butyl-4-hydroxyphenyl)propionic acid, 6,6′-ethylidene-bis(2,4-di-tert-butylphenol), 6,6′-methylene-bis(2,4-di-tert-butylphenol) and 1,3,4-tris(4-tert-butyl-3-hydroxy-2,6-dimethylbenzyl) isocyanurate.

14. A method for stabilizing an organic material against oxidative, thermal and actinic degradation which comprises incorporating into said organic material an effective stabilizing amount of a polymer according to claim 1.

* * * * *